(12) United States Patent
Librett et al.

(10) Patent No.: US 11,141,552 B2
(45) Date of Patent: Oct. 12, 2021

(54) SYSTEMS AND METHODS FOR PROVIDING LOW-NOISE POSITIVE AIRWAY PRESSURE

(71) Applicants: HUMAN DESIGN MEDICAL, LLC, Charlottesville, VA (US); Kevin Scott Librett, Watertown, MA (US); Karl R Leinsing, Dover, NH (US)

(72) Inventors: Kevin Scott Librett, Watertown, MA (US); Karl R Leinsing, Dover, NH (US)

(73) Assignee: BREAS MEDICAL, INC., North Billerica, MA (US)

( * ) Notice: Subject to any disclaimer, the term of this patent is extended or adjusted under 35 U.S.C. 154(b) by 849 days.

(21) Appl. No.: 14/776,771

(22) PCT Filed: Mar. 17, 2014

(86) PCT No.: PCT/US2014/030705
§ 371 (c)(1),
(2) Date: Sep. 15, 2015

(87) PCT Pub. No.: WO2014/145869
PCT Pub. Date: Sep. 18, 2014

(65) Prior Publication Data
US 2016/0015919 A1 Jan. 21, 2016

Related U.S. Application Data

(60) Provisional application No. 61/798,367, filed on Mar. 15, 2013, provisional application No. 61/798,541, (Continued)

(51) Int. Cl.
*A61M 16/00* (2006.01)
*F04D 29/66* (2006.01)
(Continued)

(52) U.S. Cl.
CPC .... *A61M 16/0078* (2013.01); *A61M 16/0066* (2013.01); *A61M 16/0069* (2014.02);
(Continued)

(58) Field of Classification Search
CPC .......... A61M 16/0066; A61M 16/0069; A61M 2205/42; F04D 29/663; F04D 29/664;
(Continued)

(56) References Cited

U.S. PATENT DOCUMENTS 2,176,319 A    10/1939  Anderson
3,286,787 A *  11/1966  Wirt ........................ F01D 25/30
                                                              181/213
(Continued)

*Primary Examiner* — Michael J Tsai
(74) *Attorney, Agent, or Firm* — Yi Liu

(57) ABSTRACT

The application discloses a noise attenuating system (100, 200, 300, 400, 700, 800) for use with a positive airway pressure system providing a flow of gas, comprising: an expansion chamber (140, 240, 340, 434, 740) having a volume; an intake tube (115, 215, 315, 415, 715, 815) having an inlet (117, 217, 317, 410, 717, 812) and outlet port or portion separated by a length, wherein a portion of the inlet port or portion extends outside of the expansion chamber; and either: a noise attenuator (110, 120, 170, 210, 220, 223, 224, 226, 228, 232, 270, 320, 411, 413, 422, 423, 424, 425, 426, 428, 431, 720, 722) having a bottom and protruding sidewall forming a cavity, wherein the noise attenuator is positioned near the inlet portion of the intake tube such that a portion of the intake tube extends into the cavity of the noise attenuator; or: an acoustic deflector (110, 120, 170, 210, 220, 223, 224, 226, 228, 270, 232, 320, 411, 413, 422, 423, 424, 425, 426, 428, 431, 720, 722) positioned near the outlet port or portion of the intake tube, wherein noise is deflected away from the outlet port or portion of the intake tube. The application also discloses positive air pressure apparatus (100, 200, 300, 400, 700, 800) comprising a housing (180, 480, 880, 884), first and second acoustic
(Continued)

chambers, an intake vent or port (125, 225, 410, 812) in the first chamber, an inlet port or tube coupling the first and second chambers, a noise attenuator in the first chamber, and a blower unit (150, 250, 350, 440) in the second chamber.

12 Claims, 8 Drawing Sheets

Related U.S. Application Data filed on Mar. 15, 2013, provisional application No. 61/798,462, filed on Mar. 15, 2013.

(51) Int. Cl.
  *A61M 16/08* (2006.01)
  *A61M 16/10* (2006.01)
(52) U.S. Cl.
  CPC .... *A61M 16/0816* (2013.01); *A61M 16/0858* (2014.02); *A61M 16/0875* (2013.01); *A61M 16/107* (2014.02); *F04D 29/663* (2013.01); *F04D 29/664* (2013.01); *F04D 29/665* (2013.01); *A61M 16/0063* (2014.02); *A61M 2016/0027* (2013.01); *A61M 2205/3355* (2013.01); *A61M 2205/42* (2013.01); *A61M 2205/50* (2013.01); *A61M 2205/502* (2013.01); *A61M 2205/505* (2013.01); *A61M 2205/75* (2013.01); *A61M 2205/8206* (2013.01); *A61M 2207/00* (2013.01)
(58) Field of Classification Search
  CPC ...... F04D 29/665; G10K 11/02; G10K 11/04; G10K 11/16; G10K 11/161; F05D 2260/96
  See application file for complete search history.

(56) References Cited

U.S. PATENT DOCUMENTS

| | | | |
|---|---|---|---|
| 4,590,951 A | 5/1986 | O'Connor | |
| 4,905,789 A | 3/1990 | Francis | |
| 4,971,052 A | 11/1990 | Edwards | |
| 5,984,045 A * | 11/1999 | Maeda | F01N 1/02 181/254 |
| 6,158,082 A | 12/2000 | Beckey et al. | |
| 6,342,005 B1 | 1/2002 | Daniels et al. | |
| 6,581,595 B1 | 6/2003 | Murdock et al. | |
| 6,615,831 B1 | 9/2003 | Tuitt et al. | |
| 7,112,038 B2 | 9/2006 | Curtis et al. | |
| 8,006,691 B2 | 8/2011 | Kenyon et al. | |
| 8,375,944 B2 | 2/2013 | Kwok | |
| 8,579,077 B2 * | 11/2013 | Ahn | F01N 13/08 181/212 |
| 8,783,413 B1 | 7/2014 | Thawani et al. | |
| 8,931,481 B2 | 1/2015 | Jones et al. | |
| 9,132,252 B2 | 9/2015 | Barlow et al. | |
| 2005/0166921 A1 | 8/2005 | DeVries et al. | |
| 2006/0037814 A1 * | 2/2006 | Mabuchi | F01N 1/084 181/272 |
| 2006/0237013 A1 | 10/2006 | Kwok | |
| 2007/0169781 A1 | 7/2007 | Tang | |
| 2008/0257346 A1 * | 10/2008 | Lathrop | A61M 16/0066 128/204.17 |
| 2008/0257347 A1 | 10/2008 | Grasmuck | |
| 2009/0178879 A1 | 7/2009 | Park et al. | |
| 2010/0006097 A1 | 1/2010 | Frater et al. | |
| 2011/0200426 A1 | 8/2011 | Takano | |
| 2012/0167879 A1 | 7/2012 | Bowman et al. | |
| 2014/0299130 A1 | 10/2014 | Librett et al. | |
| 2015/0176860 A1 | 6/2015 | Hattan et al. | |

\* cited by examiner

SYSTEMS AND METHODS FOR PROVIDING LOW-NOISE POSITIVE AIRWAY PRESSURE

CROSS-REFERENCE TO RELATED APPLICATIONS

This application claims the benefit of U.S. Patent Application 61/798,367 filed on Mar. 15, 2013; U.S. Patent Application 61/798,541 filed on Mar. 15, 2013 and U.S. Patent Application 61/798,462 filed on Mar. 15, 2013 which are incorporated herein by reference.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

The present invention relates to a positive airway pressure [PAP] devices, such as continuous positive airway pressure [CPAP] devices, and more particularly a method for attenuating the noise released therefrom.

2. Description of the Prior Art

It is known that applying a CPAP device to a patient may prevent upper airway occlusion during sleep. CPAP devices have become the apparatus of choice for the treatment of chronic sleep apnea, chronic pulmonary obstruction and snoring. Many CPAP machines are readily available in the marketplace.

A typical CPAP system generally includes a bedside generator comprising, a blower unit powered by an electric motor. The blower unit, the motor, and associated controls are usually encased together within the bedside generator. A delivery tube, usually a flexible plastic tube having a proximal end and a distal end, is used to deliver pressurized air or other gasses to the patient. The proximal end of the delivery tube is connected to the bedside generator and the distal end of the delivery tube is fitted to the face of a patient. The patient interface may include features that allow the patient interface to be affixed to the patient and maintain a proper orientation with respect to the patient.

Bedside CPAP machines are typically large and heavy. They are usually plugged into a wall outlet for power or have a large external battery. The size, weight, and power constraints can interfere with patients' ability and willingness to use the machine. For example, these constraints can make it difficult to utilize the CPAP apparatus in areas away from their bedside or while traveling. Additionally, these constraints can also prohibit patients from moving freely during sleep, thereby inducing further discomfort.

Furthermore, typical CPAP devices are relatively loud and can interfere with a patient's sleep or the sleep of other people nearby. In a typical CPAP device, sound may be propagated from various locations and actions of the device, such as the flow of air the flow of air into and out of the device or the operation of the motor and fan. Because the apparatus is used mainly in a bedroom or other place having a low ambient noise level to facilitate sleep, it is important that the blower operates quietly so as not to disturb the patient or others in close proximity while they sleep.

A need therefore exists for PAP devices with size, weight, and sound characteristics that provide improved usability for patients.

SUMMARY OF THE INVENTION

The system and methods described herein provide a CPAP apparatus that can be held and operated in one hand, is portable, and is quieter than 30 decibels (dBA) while in operation.

In an exemplary embodiment, the current application discloses a CPAP apparatus having an air intake attenuator comprising: an intake attenuation chamber defining at least one intake slot; an acoustic chamber having an inlet port and at least one acoustic deflector; a motor or blower that is placed within the acoustic chamber, wherein vibrations from the motor or blower are isolated or substantially isolated from the single chamber; and in some embodiments a dissipative element that may be added to further attenuate the amount of noise heard by the patient.

A noise attenuating system for use with ventilation or other systems providing a flow of gas comprising an expansion chamber having a volume; an intake tube having an inlet and outlet port separated by a length, wherein a portion of the inlet port extends outside of the expansion chamber; and a noise attenuator having a bottom and protruding sidewall forming a cavity, wherein the noise attenuator is positioned over the inlet portion of the intake tube such that a portion of the intake tube extends into the cavity portion of the noise attenuator.

The system may further include the intake tube having a length that ranges from 0.25 inches to 3.5 inches.

The system may further comprise a plurality of acoustic deflectors disposed within the cavity portion of the noise attenuator.

The system may include at least one deflector that extends from the sidewall and is aligned substantially parallel to the bottom of the noise attenuator.

The system may further include at least one deflector that extends from the sidewall and is angled into the cavity of the noise attenuator.

The system may further comprise a noise dissipating element disposed within the cavity portion of the noise attenuator.

The system may further include a noise dissipating element that is a porous material and at least one acoustic deflector that is covered by a noise dissipating material. The expansion chamber may have an acoustic deflector positioned near the outlet portion of the intake tube the acoustic deflector is angled with respect to a plane defining the outlet portion of the intake tube. In some cases the system include positioning the back-side of the acoustic deflector to deflect noise emanating from a region within the expansion chamber having the greatest noise intensity, wherein the noise is deflected away from the outlet port of the intake tube.

These and other embodiments are described in more detail herein.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION OF THE PREFERRED EMBODIMENT

To provide an overall understanding of the systems, devices, and methods described herein, certain illustrative embodiments will be described. Although the embodiments and features described herein are frequently described for use in connection with CPAP apparatuses, systems, and methods, it will be understood that all the components, mechanisms, systems, methods, and other features outlined below may be combined with one another in any suitable manner and may be adapted and applied to other PAP apparatuses, systems, and methods, including, but not limited to, automatic positive airway pressure devices [APAP], variable positive airway pressure devices [VPAP], bi-level positive airway pressure devices [BPAP], and related apparatuses, systems, and methods.

Bedside CPAP machines are typically large, heavy, and noisy. The systems and methods described herein are directed towards a small, quiet, light-weight, and portable CPAP device to overcome these current limitations and disadvantages. For example, the systems and methods described herein provide a PAP apparatus that is quieter than 30 decibels (dBA) while in operation. In certain approaches, the PAP apparatus can be held and operated in one hand and is portable.

Figure 1:
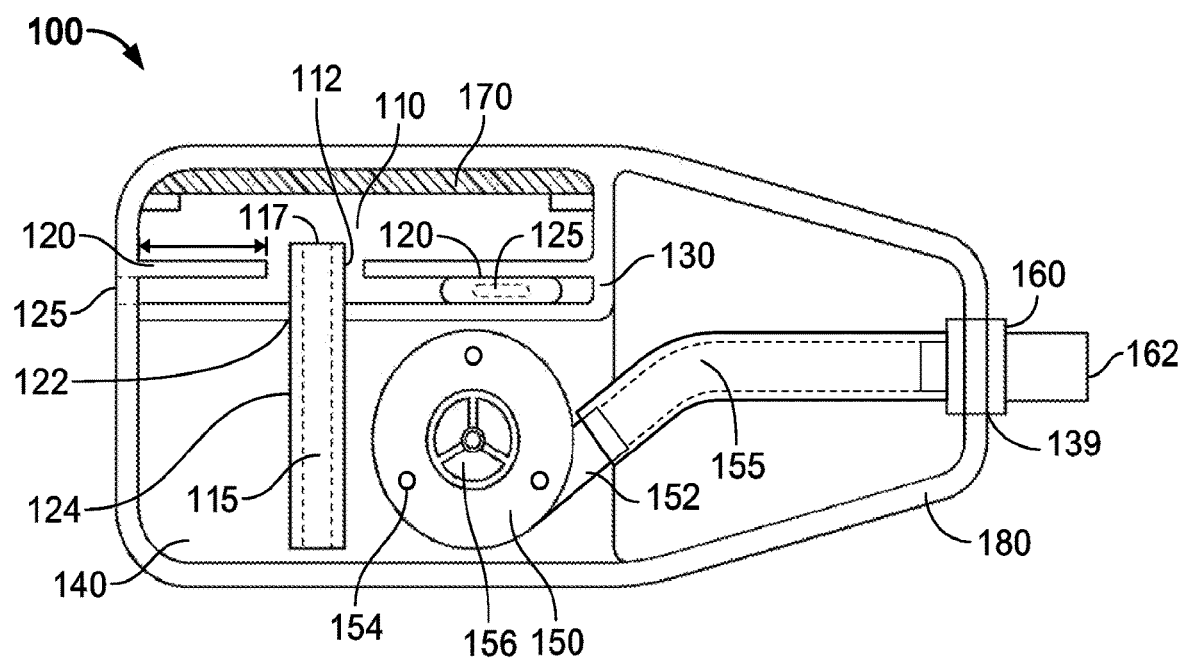
FIG. 1 illustrates the interior of a portable PAP apparatus.

FIG. 1 depicts the interior of a PAP apparatus, such as a CPAP device. CPAP device 100 has a lower housing component 180, which together with an upper housing component (not shown) defines a sealed chamber 140. PAP apparatus 100 includes an intake chamber 110 positioned on a side or back of apparatus 100.

Intake chamber 110 serves to prevent the occlusion of inlet port 122 during use of device 100. Intake chamber 110 may also reduce the acoustic output or noise of apparatus 100. For example, intake chamber 110 includes foam 170 to reduce acoustic output of apparatus 100. Although foam is described, any dissipative element could be used. Dissipative elements may include anechoic materials such as foam, rubber, clay, silicon, or any other suitable soft and/or porous materials. Additionally or alternatively, apparatus 100 includes intake vents 125, through which air may flow. In the depicted example, intake vents 125 are positioned at the side, top, and/or bottom of apparatus 100.

Both the attenuation intake chamber and the acoustic chambers may be designed to reduce the amount of noise released from the CPAP device during operation. Intake chamber 110 includes sound attenuators 120 positioned within intake chamber 110. For purposes of the systems and methods described herein, an attenuator may refer to any of a plane, bar, circular, semi-circular, sphere, cone, or other mechanism configured to deflect, absorb, weaken and/or reduce a sound wave.

Although two attenuators 120 are depicted in FIG. 1, any number of attenuators may be used. In some embodiments, the upper and lower housing components and/or the chamber wall 130 define a plurality of attenuators 120 extending therefrom. For example, the flow path defined by attenuators 120 in FIG. 1 includes one right-angle turn. In additional embodiments however, the upper and lower housing components may define a variety of attenuators. For example, the housing components may be configured such that the flow path defines any number of turns each of any angular dimension (e.g., sixty degrees, ninety-degrees, one-hundred-eighty degrees, etc.) and any combination of vertical and horizontal turns. While the attenuator 120 may divert the airflow pathway and thereby create additional broadband noise, the primary purpose of the attenuator(s) is to reduce the amount of noise exiting the CPAP device. In embodiments having more than one attenuator 120, each of attenuator 120 may have the same size and length, and may be defined by the housing components to have the same or substantially similar angles relative to the inlet port, chamber wall, and/or housing components. Alternatively, each attenuator 120 may have different sizes, shapes, and/or lengths. Further, each attenuator 120 may be oriented having varying angles relative to the inlet port chamber wall, and/or housing components and in some instances one or more attenuators 120 may partially or substantially surround the inlet port 122. In certain approaches, one side of chamber 110 may have more attenuators 120. Additionally or alternatively, chamber 140 may include attenuators 120.

Sealed chamber 140 has an inlet port 122 and an outlet port 139. Inlet port 122 is positioned in wall 130, which separates intake chamber 110 and sealed chamber 140. A motor or blower 150 is placed within the chamber 140. An intake tube 115 extends from intake chamber 110, through inlet port 122, and into acoustic chamber 140. Intake tube 115 includes opening 117 to enable air flow from intake chamber 110 into acoustic chamber 140. Although depicted as straight, intake tube 115 may include any number of turns.

In some embodiments, foam or another anechoic material may be placed within chamber 130 to further attenuate noise produced during the operation of device 100. The anechoic or noise attenuating material may be secured at specific locations within each chamber. In additional embodiments, the lower and/or upper housing components may be lined with an anechoic or noise attenuating material. In such embodiments, the anechoic or noise attenuating material may include foam, rubber, clay, silicon, or any other suitable soft and/or porous materials.

In certain embodiments, blower 150 is secured to chamber 140 using one or more mount connects 154. In some embodiments, the mount connects may further comprise pivoting cone connectors, circular donut shaped mount connects, a silicone cradle, or any combination thereof. For example, the mount connects may comprise pivoting cone connectors that connect the top of blower 150 within chamber 140 and circular donut shaped mount connects that connect the bottom of blower 150 within chamber 140. In addition to connecting blower 150 to the housing, mount connects 154 may reduce or eliminate transfer of vibrations from the blower to other components of device 100. In certain embodiments, blower 150 is a brushless air-bearing motor.

In certain embodiments, inlet port 122 includes an intake tube 115 having a first end 112 through wall 130 and a second end 124 that extends into chamber 140. Intake tube 115 may have either a constant or varying internal diameter ranging from approximately 0.25 inches to approximately 0.75 inches and may have a length ranging from approximately 0.25 inches to approximately 3 inches, although any appropriate diameter and length may be used. The length and diameter of intake tube 115 affect the overall noise attenuation of the CPAP device, as will be further discussed below, for example, in relation to FIG. 2 and equation 1 and equation 2. Accordingly, in some approaches, the dimensions of intake tube 115 are proportionally related to the volume of chamber 140.

Intake tube 115 may be formed using rigid materials, flexible materials, or any combination thereof. For example, intake tube 115 may be formed using a hard plastic. In certain embodiments, intake tube 115 is composed of flexible polyvinylchloride (PVC) tubing, silicone tubing, or any other type of tubing commonly used in the art.

In certain approaches, outlet port 139 includes outlet tube 155, which extends from blower outlet 152 and through the housing, such as lower housing 180. An adapter 160 may be used to connect the blower outlet tube 145 to a patient interface, such as mask that can be coupled to the airways (e.g., nose and mouth) of a patient. In embodiments having adapter 160, adapter 160 may be solitary in construction. Additionally or alternatively, adapter 160 may be configured so that a proximal portion of adapter 160 is secured and sealed to the housing of device 100, while a distal portion of the adapter 160 extends outward from device 100. In such an embodiment, lower housing component 180 and the upper housing component may each include a detent capable of accepting a portion of the adapter, whereby the two housing components together form a seal around the circumference of a portion of the adapter.

Outlet tube 155 may also vary in length and diameter. The length of the blower outlet tube 155 is long enough to connect to outlet 152 of blower 150 through outlet port 139. Outlet tube 155 provides a sealed airway between blower 150 and adapter 160. Additionally, depending on the dimensions of the blower 150, the inner diameter of the outlet tube 155 may vary so long as the diameter is large enough to fit over and seal with outlet 152 and adapter 160 and/or a patient interface system, such as tubing and a delivery mask. Outlet tube 155 may be formed using rigid materials, flexible materials, or any combination thereof. For example, outlet tube 155 may be formed using a hard plastic. In certain embodiments, outlet tube 55 is composed of flexible polyvinylchloride (PVC) tubing, silicone tubing, or any other type of tubing commonly used in the art.

In certain embodiments, intake chamber 110 may include a filter to clean the air of particulate matter. In certain embodiments, intake chamber 110 is removable from chamber 140 and other components of device 100 so that chamber 110 may be cleaned, replaced, or adapted for a particular need. For example, various types of filters may be used depending on a patient's health needs. A filter may not be required for all patients, may be replaceable, or may be cleaned.

During operation, PAP device 100 creates positive air pressure through outlet port 139. For example, when a patient interface, such as a mask, is attached, PAP device 100 creates positive air pressure, which can be provided to the patient when the patient places the patient interface at his or her airways (e.g., nose or mouth). Blower 150 includes intake 156. When blower 150 is powered on, blower 150 intakes air through intake 156 and pushes out that air through outlet 152. The reduced pressure at intake 156 causes air to flow through vents 125, into chamber 110, through inlet port 122 via tube 115, and into chamber 130, where it then flows into intake 156 of blower 150. Blower 150 then pushes air through outlet 152, through outlet tube 155, and through outlet port 139 to thereby provide positive air pressure through outlet port 139, for example, through hole 162 of adapter 160. In certain approaches, the pressurized air is delivered a pressure ranging from approximately 2 centimeters (cm) of water to approximately 40 cm of water above atmospheric pressure at the point of use, although any appropriate pressure may be used.

FIG. 2 depicts the interior of a portable PAP apparatus 200. PAP apparatus 200 includes an attenuation intake chamber 210 with sound attenuators 220 positioned within intake chamber 210. In certain approaches, intake chamber 210 includes foam 210 to the reduce acoustic output or noise of apparatus 200. Although foam is described, any dissipative element could be used. Dissipative elements may include anechoic materials such as: foam, rubber, clay, silicon, or any other suitable soft and/or porous materials. Additionally or alternatively, apparatus 200 includes intake vents 225, through which air may flow.

PAP apparatus 200 has an acoustic chamber 240 with an inlet port 222 coupled to intake chamber 210. An intake tube 215 extends from intake chamber 210, through inlet port 222, and into acoustic chamber 240. Intake tube 215 includes opening 217 to enable air flow from intake chamber 402 into acoustic chamber 240. When in operation, blower 150 is powered on and pulls air through vents 225, into opening 217, through tube 215, and into blower 250. Blower 250 then pushes air through outlet tube 255 and through opening 262 into a patient interface, such as a respiratory mask.

The size and location of intake tube 215 and opening 217 may be determined based on the location and size of the attenuators 220. For example, opening 217 may have a diameter of approximately 0.5 inches and intake tube 215 may extend into attenuating intake chamber 210 approximately 0.875 inches beyond attenuators 220. In certain embodiments, the diameter of opening 217 along the length of intake tube 215 varies in diameter, for example, from approximately 0.25 inches to 0.75 inches. In certain embodiments, intake tube 215 extends into attenuating intake chamber 210 so that opening 217 is substantially even with attenuators 220. In certain approaches, intake tube 215 extends past attenuators 220 by more than approximately 1 inch.

Figure 2A:
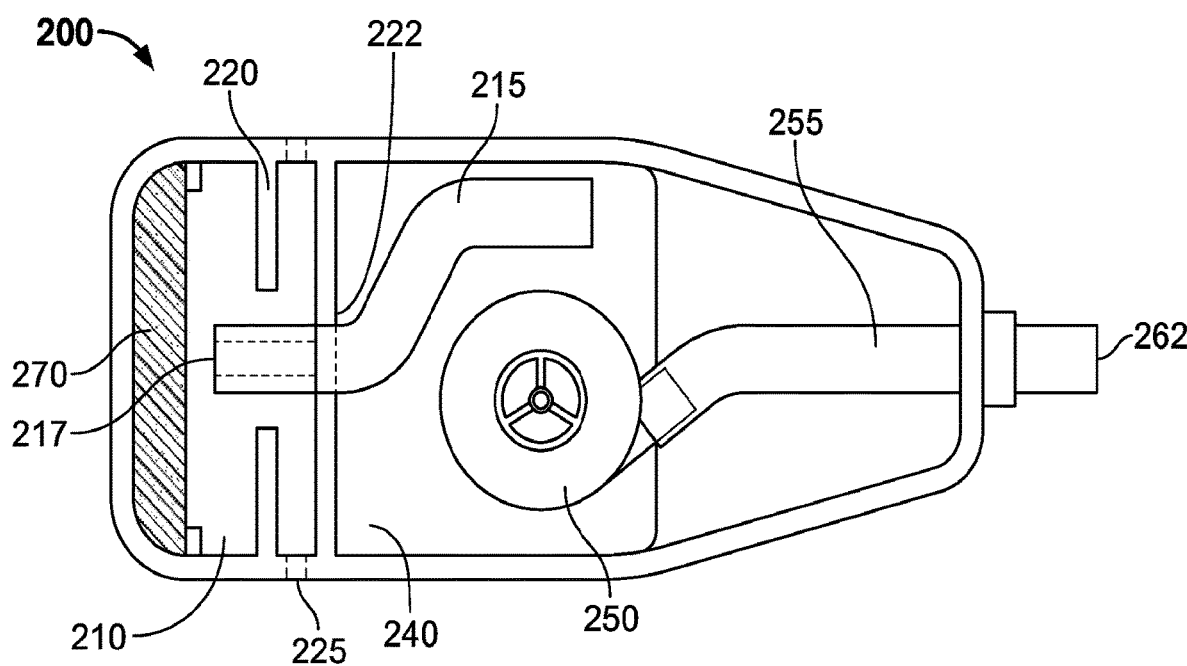
FIG. 2A depicts an interior view of a portable CPAP apparatus.
Figure 2B:
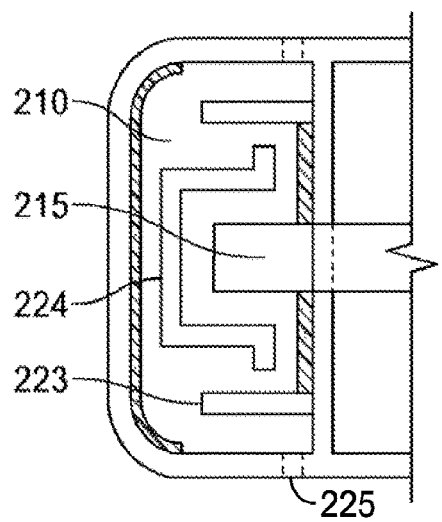
FIGS. 2B-D illustrate configurations of chamber configurations.
Figure 2C:
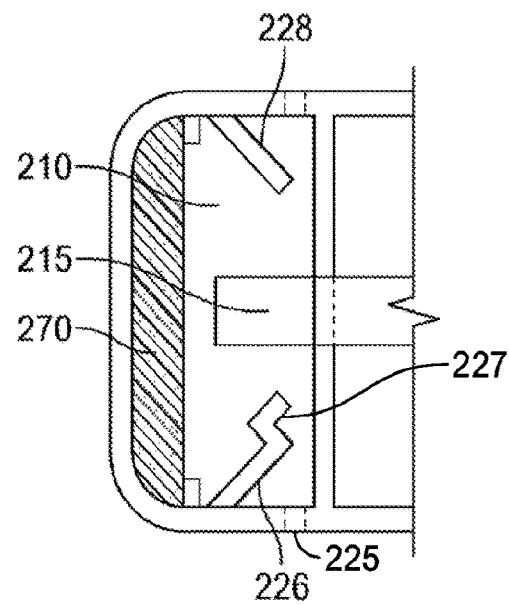
Figure 2D:
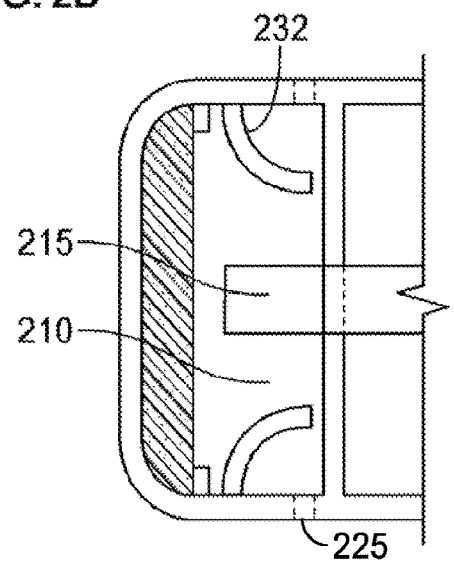

FIGS. 2B-D illustrate additional embodiments of device 200 with additional or alternative configurations of attenuators for reducing noise output. FIG. 2B depicts device 200 with attenuators 223 that are configured approximately parallel to intake tube 215. FIG. 2B also shows an end cap attenuator 224, which extends partially around intake tube 215, but does not directly contact intake tube 215. FIG. 2C depicts angled attenuators 226 and 228. Attenuators 226 and 228 extend at an angle relative to the side walls of device 200 and, in this example, relative to the intake tube 215. Attenuator 226 also includes an "L" extension 227, which extends from the distal end of attenuator 226. FIG. 2D shows curved attenuators 232. Each type of attenuator (220, 223, 224, 226, 228, and 232) alters the flow of air from vent 225 to blower 250. They can be used individually or in any combination. Additionally, attenuators of other shapes may also be used, such as those with additional curves, different angles, additional extensions, and combinations of curves and linear portions. The attenuators are used to create unique air flow paths, which also have the important effect of altering and reducing the noise properties of device 200.

Figure 3:
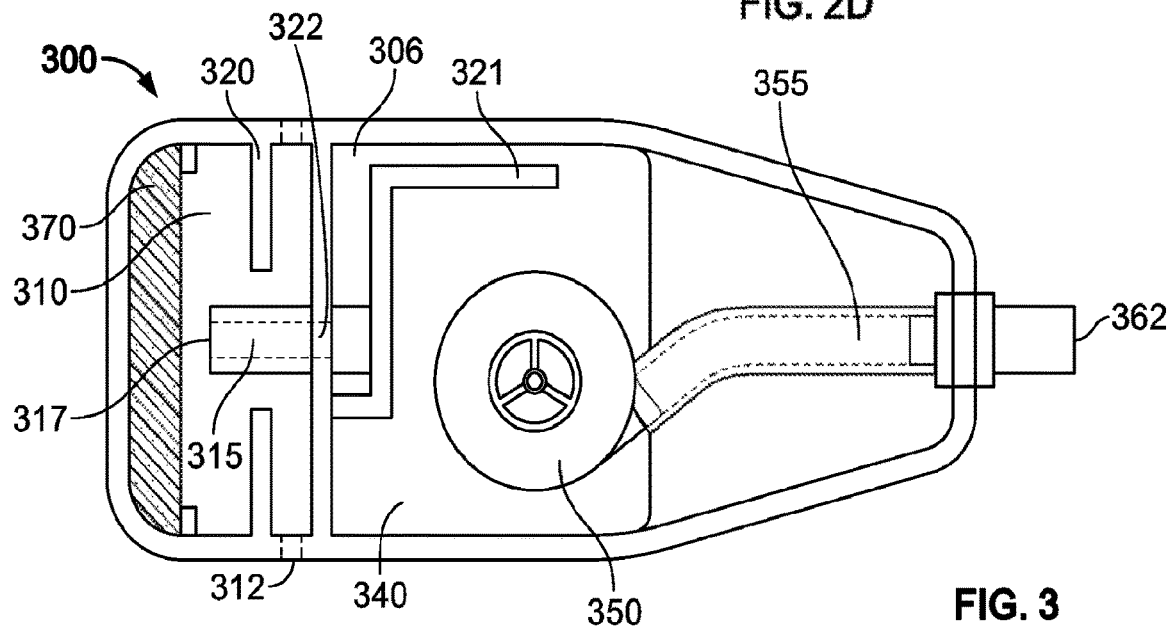
FIG. 3 depicts an example of the interior of a portable PAP apparatus.

FIG. 3 depicts the interior of a portable PAP apparatus 300. PAP apparatus 300 includes an attenuation intake chamber 310 with sound attenuators 320 positioned within intake chamber 310. In certain approaches, intake chamber 310 includes foam 370 to reduce the acoustic output of apparatus 300. Although foam is described, any dissipative element could be used. Dissipative elements may include anechoic materials such as: foam, rubber, clay, silicon, or any other suitable soft and/or porous materials. Additionally or alternatively, apparatus 300 includes intake vents 312, through which air may flow.

PAP apparatus 300 has an acoustic chamber 340 coupled to intake chamber 310 via inlet port 322. In certain approaches, apparatus 300 includes a first intake tube 315 extending into intake chamber 310. Apparatus 310 includes a barrier 321 within chamber 340, which forms flow space 306, which is in fluid communication with first intake tube 315. As depicted, flow space 306 can have turns or bends. Barrier 321 may be configured such that flow space 306 defines any number of turns, wherein each turn has of any angular dimension (e.g., sixty degrees, ninety-degrees, one-hundred-eighty degrees, etc.) and any combination of vertical and horizontal turns. In certain approaches, barrier 321 is firm and inflexible. When in operation, blower 350 is powered on and pulls air through vents 312 into opening 317 of intake tube 315, through tube 315, through inlet port 322, through flow space 306, into acoustic chamber 340, and into blower 350. Blower 350 then pushes air through outlet tube 355 and through opening 362 into a patient interface, such as a respiratory mask.

FIG. 4 depicts the interior of a dual chamber PAP apparatus 400. CPAP device 400 has a lower housing component 480, which together with an upper housing component (not shown) defines a first sealed chamber 430 and a second sealed chamber 434 separated by wall 432. First sealed chamber 430 has an inlet port 410 with intake tube 415, which extends through housing 480, through second chamber 434, and through wall 432 into first chamber 430. A first portion 412 of tube 415 is outside housing 480 and a second portion 420 is inside sealed chamber 430. In some embodiments, the first chamber may further include a noise attenuator 431 positioned within the airflow path from portion 420 of intake tube 415.

Device 400 includes an interchamber port 417, which allows air to flow from the first chamber 430 to the second chamber 434. In certain approaches, interchamber port 417 includes a tube 416, which extends from first chamber 430, through chamber wall 432, and into second chamber 434.

The first and second chambers are separated by a chamber wall 432. In some embodiments, chamber wall 432 may be formed on lower housing and/or the upper housing (not depicted). In certain approaches, chamber wall 432 is solitary in construction with the housing. Additionally or alternatively, chamber wall 432 may be secured to the respective housing components with an adhesive or glue. Additionally, chamber wall 432 may be formed from an anechoic material such as foam, rubber, clay, silicon, or any other suitable soft and/or porous materials. In certain embodiments, chamber wall 432 may be formed using a rigid material, such as a hard plastic.

A motor or blower 440 is located within second chamber 434. In certain embodiments, blower 440 is secured to chamber 434 using one or more mount connects 450. In some embodiments, the mount connects may further comprise pivoting cone connectors, circular donut shaped mount connects, a silicone cradle, or any combination thereof. For example, the mount connects may comprise pivoting cone connectors that connect the top of blower 440 within chamber 434 and circular donut shaped mount connects that connect the bottom of blower 440 within chamber 430. In addition to connecting blower 440 to the housing, mount connects 440 may reduce or eliminate transfer of vibrations from the blower to other components of device 400. In certain embodiments, blower 440 is a brushless air-bearing motor.

In some embodiments, foam or another anechoic material may be placed within chamber 430 and chamber 434 to further attenuate noise produced during the operation of device 400. The anechoic or noise attenuating material may be secured at specific locations within each chamber. In additional embodiments, the lower and/or upper housing components may be lined with an anechoic or noise attenuating material. In such embodiments, the anechoic or noise attenuating material may include foam, rubber, clay, silicon, or any other suitable soft and/or porous materials.

In at least one embodiment, the first chamber 430 further comprises an attenuator 431 which may be placed within the chamber directly across from the proximal end 420 of intake tube 415. Attenuator 431 is positioned within the airflow path to thereby attenuate noise created by the flow of air through chamber 430. In certain approaches, attenuator 431 is angled toward the intake tube having an acute angle relative to the housing component. In certain approaches, device 400 includes a plurality of attenuators. In certain approaches, device 400 includes at least attenuator in second chamber 434. When a plurality of attenuators are included, each attenuator, such as attenuator 431, within the chamber 430 or chamber 434 may be oriented in varying angles relative to the end of intake tube 415, interchamber tube 416, and/or the housing components. While the attenuators may vary in size, length, quantity, shape, angle, and/or location, they may divert the airflow pathway and thereby create additional broadband noise, the primary purpose of attenuators is to reduce the amount of noise exiting the CPAP device. Attenuators may further comprise a dissipative element, noise attenuating coating, and/or a noise attenuating material attached thereto. For example, attenuator 431 may be composed of or coated with an anechoic or noise attenuating material. The anechoic or noise attenuating material may include foam, rubber, clay, silicon, or any other suitable soft and/or porous materials.

Device 400 additionally includes one or more connector portions 485 to couple lower housing 480 and upper housing together, thereby creating a seal. In the depicted example, the connector portions 485 are around the perimeter of the housing and a fastener, such as a screw, is used to couple the housing. Additionally or alternatively, the edge 482 of the housing may provide a coupling and/or sealing mechanism. For example, edge 482 has a tongue, which may couple to a groove in an upper housing portion. Edge 182 may also include a seal, such as santoprene or silicone.

Intake tube 415 and interchamber tube 416 may have either a constant or varying internal diameter ranging from approximately 0.25 inches to approximately 0.75 inches and may have a length ranging from approximately 0.25 inches to approximately 3 inches, although any appropriate diameter and length may be used. The length and diameter of intake tube 415 affect the overall noise attenuation of the CPAP device, as further discussed in relation to FIG. 5 and equation 1 and equation 2. Accordingly, in some approaches, the dimensions of intake tube 415 and interchamber tube 416 are proportionally related to the volume of chamber 430.

Intake tube 415 and interchamber tube 416 may be formed using rigid materials, flexible materials, or any combination thereof. For example, intake tube 415 and interchamber tube 416 may be formed using a hard plastic. In certain embodiments, intake tube 415 and interchamber tube 416 are composed of flexible polyvinylchloride (PVC) tubing, silicone tubing, or any other type of tubing commonly used in the art. Intake tube 415 and interchamber tube 416 may be composed of different materials.

In certain approaches, outlet port 439 includes outlet tube 445, which extends from blower outlet 437 in second chamber 434, through wall 432, through first chamber 430, and through housing 480. An adapter 460 may be used to connect the blower outlet tube 445 to patient interface 465. In embodiments having an adapter, the adapter may be solitary in construction and configured so that a proximal portion of the adapter may be secured and sealed to the housing of device 400, while a distal portion of the adapter extends outward from device 400. In such an embodiment, the lower housing component 480 and the upper housing component may each include a detent capable of accepting a portion of the adapter, whereby the two housing components together form a seal around the circumference of a portion of the adapter.

Outlet tube 445 may also vary in length and diameter. The length of the blower outlet tube 445 is long enough to connect to outlet 437 of blower 440 through outlet port 439. Outlet tube 445 provides a sealed airway between blower 440 and adapter 460 and/or patient interface system 465. Additionally, depending on the dimensions of the blower 440, the inner diameter of the outlet tube 445 may vary so long as the diameter is large enough to fit over and seal with outlet 437 and adapter 460 and/or patient interface system 465. Outlet tube 445 may be formed using rigid materials, flexible materials, or any combination thereof. For example, outlet tube 445 may be formed using a hard plastic. In certain embodiments, outlet tube 445 is composed of flexible polyvinylchloride (PVC) tubing, silicone tubing, or any other type of tubing commonly used in the art.

Apparatus 400 includes a pressure port 462. Pressure port 462 is coupled to adapter 460. Pressure port 462 runs through housing 480 into chamber 430, where pressure port 462 couples to a pressure sensor, such as a pressure sensor on circuitry board 444. Pressure port 462 provides fluid communication from the output of device 400 at adapter 460 to a pressure sensor coupled to control circuitry. Circuitry board 444 includes control circuitry and control components for the operation of device 400. Circuitry board 444 may be positioned over or under outlet tube 445. In certain approaches, circuitry board 444 includes a power sources, such as a power adapter or battery. In certain approaches, the control circuitry on board 444 of device 400 is configured to display the pressure measured through pressure port 462 at a display, such as display 888 depicted in FIG. 8. In certain embodiments, the pressure output of device 400 may be adjusted manually by the user with user interface buttons. In certain approaches, the control circuitry on board 444 is configured to automatically adjust the output of device 400 based on the pressure measurements. The output of device 400 may be adjusted by modulating the power of blower 440.

Although not depicted, device 400 may include a cover, such as cover 890, cover 900, or cover 910, described in greater detail below, which covers and prevents the occlusion of inlet port 410

During operation, PAP device 400 creates positive air pressure through outlet port 439. For example, when patient interface 465 is attached, PAP device 400 creates positive air pressure, which can be provided to the patient when the patient places the adapter at his or her airways (e.g., nose or mouth). Blower 440 includes intake 435. When blower 440 is powered on, blower 440 intakes air through intake 435 and pushes out that air through outlet 437. The reduced pressure at intake 435 causes air to flow through inlet port 410 into chamber 430, where it then flows through interchamber port 416 into second chamber 434, and into intake 435 of blower 440. While in chamber 430, the air can flow above or below outlet tube 445. Blower 440 then pushes the air through outlet 437, through outlet tube 445, and through outlet port 439 to thereby provide positive air pressure through outlet port 439. In certain embodiments, air may be initially passed through a pre-intake chamber, such as intake chamber 110 as described in relation with device 100, before entering inlet port 410. In certain approaches, the pressurized air is delivered to a patient through a patient interface, such as a respiratory mask, at a pressure ranging from approximately 2 centimeters (cm) of water to approximately 40 cm of water above atmospheric pressure at the point of use, although any appropriate pressure may be used.

Both the first chamber 430 and second chambers 434 may be designed to reduce the amount of noise released from CPAP device 400 during operation. In such embodiments, the chambers may be designed to operate as a high-pass, low-pass, band filter, or a combination thereof. For example, in one embodiment, first chamber 430 may be designed as a low-pass filter, while second chamber 434 is designed as a high-pass filter. In additional embodiments, first chamber 430 and second chamber 434 may both operate as low-pass filters.

In certain approaches, first chamber 430 and second chamber 434 have a combined volume ranging from approximately 200 milliliters (mL) to approximately 485 mL. For example, the combined volume of first chamber 430 and second chamber 434 may be approximately 481 mL. The combined volume of first chamber 430 and second chamber 434 may be approximately 362 mL. The combined volume of first chamber 430 and second chamber 434 may be less than 200 mL.

Additionally or alternatively, first chamber 430 and second chamber 434 may have equivalent volumes. In certain approaches, one of the chambers may have a larger volume than the other chamber. For example, in an embodiment where the combined volume is approximately 270 mL, first chamber 430 may have a volume ranging from approximately 70 mL to approximately 170 mL, and second chamber 434 may have a volume ranging from approximately 100 mL to approximately 200 mL. As an additional example, in an embodiment where the combined volume is approximately 480 mL, first chamber 430 may have a volume ranging from approximately 180 to approximately 240 mL, while second chamber 434 may have a volume ranging from approximately 240 to approximately 300 mL. In some instances, the second acoustic chamber, which houses the blower, is larger than the first acoustic (or expansion) chamber.

Figure 5:
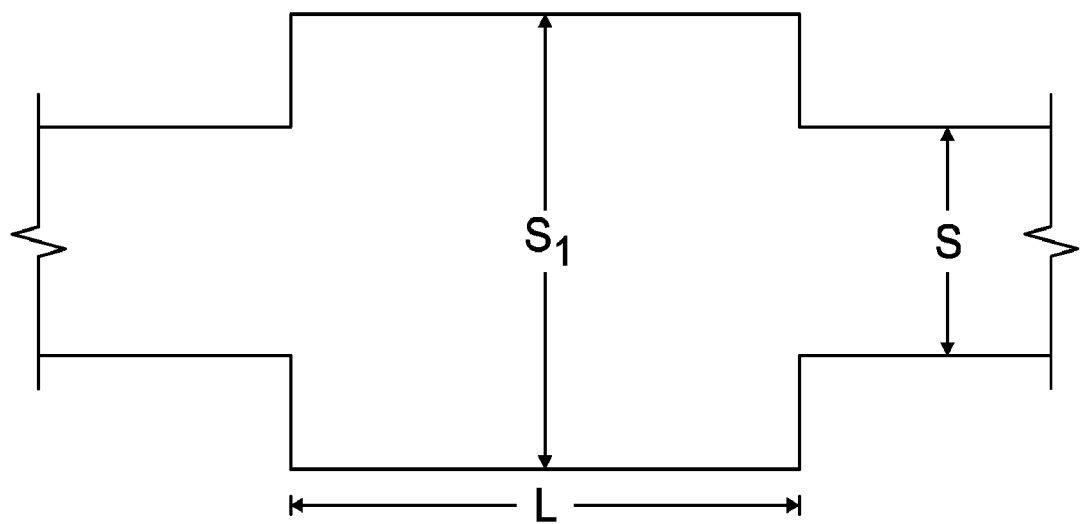
FIG. 5 illustrates the relationship between the area of an inlet port and a tube or chamber for reducing noise.

As is shown in both Equation 1 and FIG. 5, inlet port 410 and interchamber port 417 may each have an area that is proportionally related to the volume of chambers 430 and 434 respectively. In other embodiments however, inlet ports may be designed without using Equation 1.

Figure 4A:
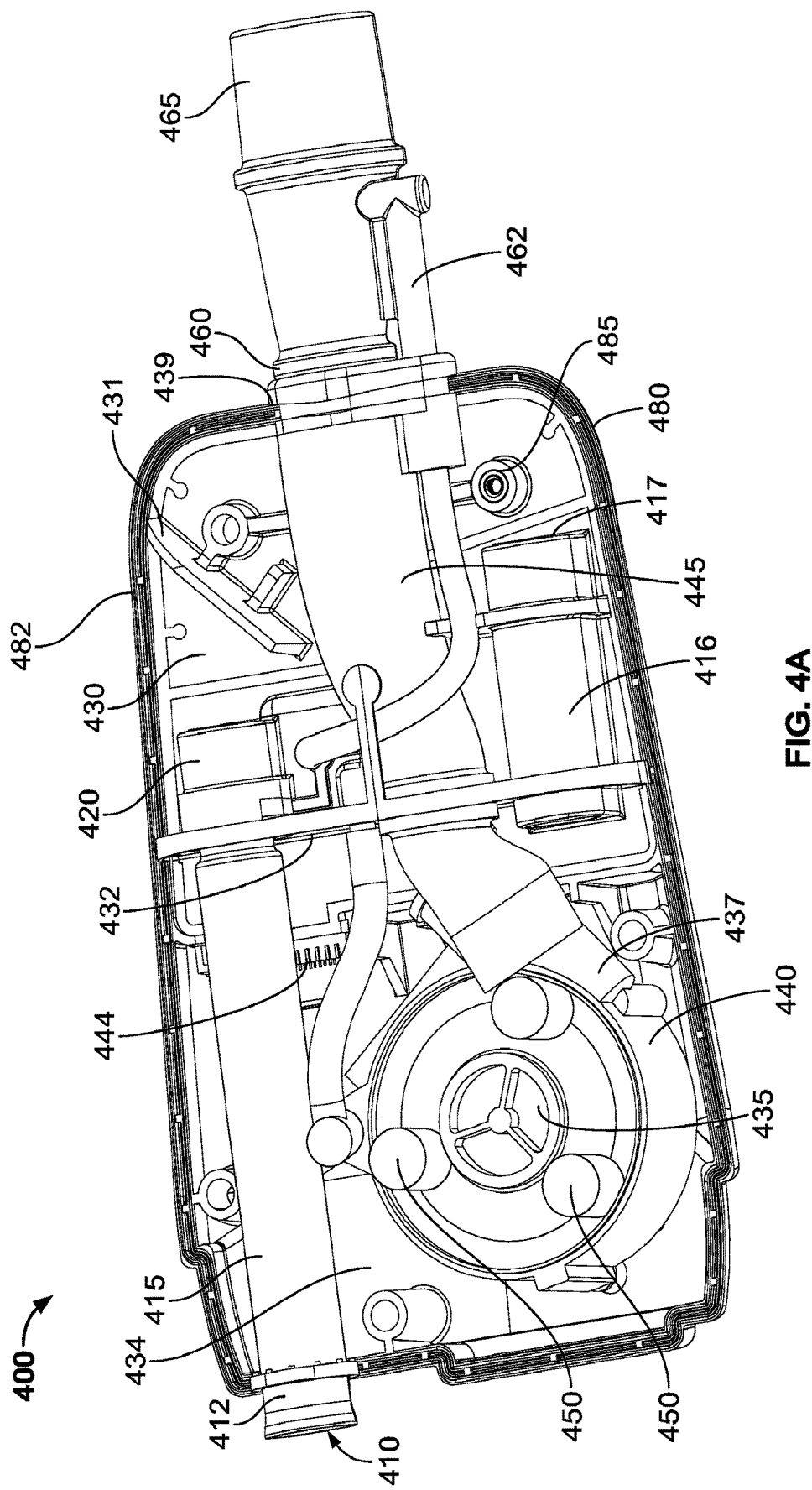
FIG. 4A illustrates a perspective view a portable dual-chamber PAP apparatus.

FIG. 4A illustrates CPAP device 400 that has a lower housing component, which together with an upper housing component (not shown) defines two sealed chambers in series, a first chamber 481 and a second chamber 482, the chambers being divided by chamber wall 483. The first chamber has an inlet port 417, which may further comprise an intake tube 416 that extends from the first chamber to the exterior of CPAP device. In some embodiments, the first chamber may further include an attenuator 420. The second chamber also has an inlet port 418 which may comprise an intake tube 416 that extends from the first chamber and into the second chamber. In the embodiment shown, the motor or blower is located within the second chamber and may be vibrationally isolated from the second chamber and/or the upper or lower housing component using mount connects 452.

Figure 4B:
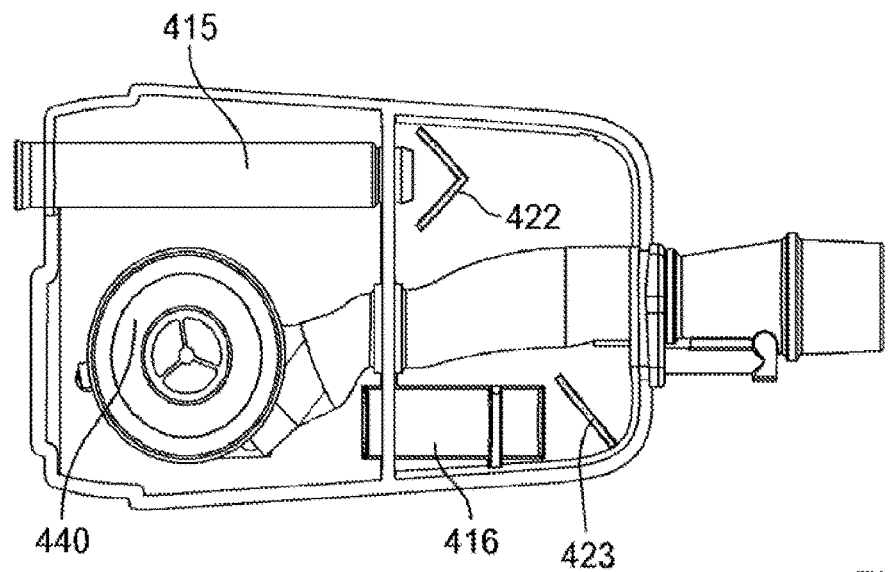
FIGS. 4B-D illustrate additional embodiments of possible attenuator configurations.
Figure 4C:
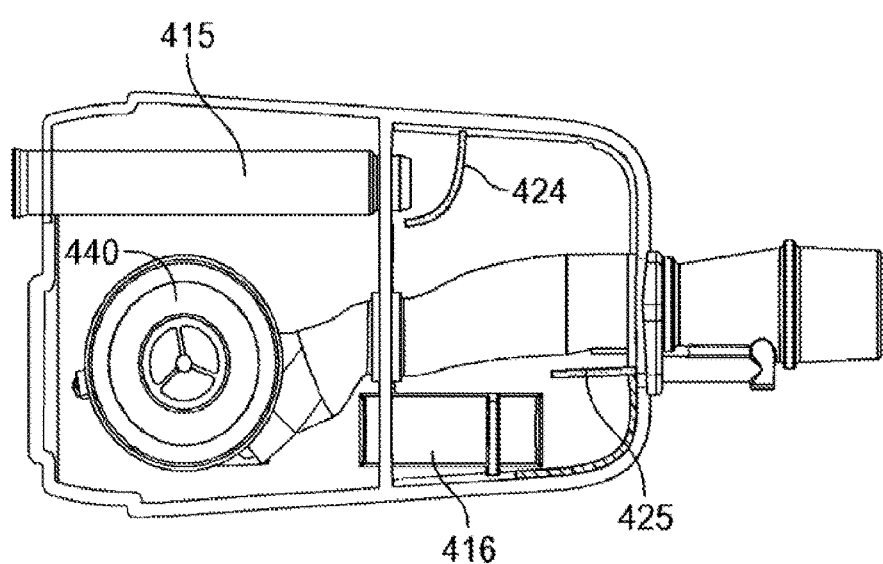
Figure 4D:
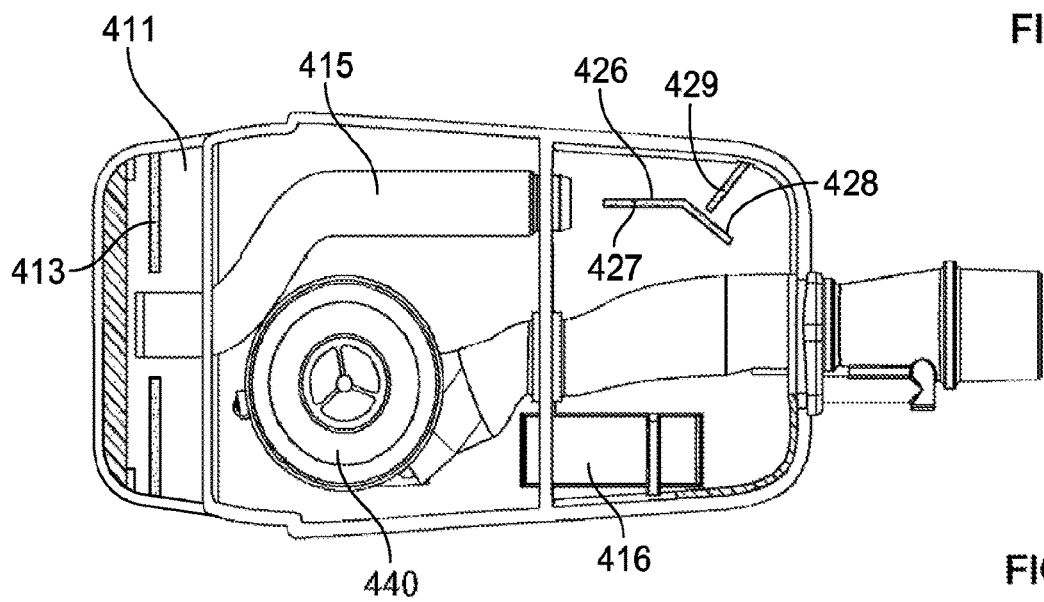

As shown, the first chamber in FIG. 4A includes an attenuator that is located within the chamber directly across from the proximal end of intake tube 115, the attenuator is angled toward the intake tube having an acute angle relative to the housing component. FIGS. 4B-D illustrate additional embodiments having a plurality of attenuators. In such embodiments, the plurality of attenuators may be located within the chamber oriented in varying angles relative to the end of the intake tubes, the noise source, and/or the housing components. While the attenuators may vary in size, length, quantity, shape, angle, and/or location, they may divert the airflow pathway and thereby create additional broadband noise, however, the primary purpose of the attenuators is to reduce the amount of noise exiting the CPAP device.

In embodiments having an attenuator, the attenuators may further comprise a dissipative element, noise attenuating coating, and/or a noise attenuating material attached thereto.

Device 100 additionally includes connector portion 185 to couple lower housing 180 and upper housing together, thereby creating a seal. In the depicted example, the connector portions 185 are around the perimeter of the housing and a fastener, such as a screw, is used to couple the housing. Additionally or alternatively, the edge 182 of the housing may provide a coupling and/or sealing mechanism. For example, edge 182 may have a tongue and groove. Edge 182 may also include a seal, such as santoprene or silicone.

FIGS. 4B-D illustrate additional embodiments of device 400 with additional or alternative configurations of attenuators for reducing noise output. FIG. 4B shows a "V" shaped attenuator 422 positioned in chamber 430 near tube 415 and angled attenuator 425 positioned in chamber 423 near interchamber tube 416. FIG. 4C depicts curved attenuator 424 positioned in chamber 430 near tube 415 and parallel attenuator 425 positioned in chamber 423 near and approximately parallel to the opening of interchamber tube 423. FIG. 4D depicts attenuator 426 and attenuator 429 positioned in chamber 430 near tube 415. Attenuator 426 has a first portion 427 that is approximately parallel to tube 415. Attenuator 426 additionally includes an angled portion 428 that is angled from portion 427 and directs air approximately toward tube 416. Attenuator 429 is angled from housing 480. FIG. 4C additionally includes an intake chamber 411, which in certain approaches, is similar to previously described intake chamber 310. Intake chamber 411 includes attenuators 413.

Each type of attenuator (422, 423, 424, 425, 426, 427, 431) alters the flow of air from through device 400, for example, from intake tube 415 to interchamber tube 416. The attenuators can be used individually or in any combination. Additionally, attenuators of other shapes may also be used, such as those with additional curves, different angles, additional extensions, and combinations of curves and linear portions. The attenuators are used to create unique air flow paths, which also have the important effect of altering and reducing the noise properties of device 400. Although not depicted, similar attenuators may also be used in chamber 434, for example, near interchamber tube 416 or around blower 440.

FIG. 5 illustrates a low-pass acoustic filter system. The equation below describe the effects modifying each geometrical section of the filter system has on the system.

$$T_\pi = \left( \frac{1}{1 + \left(\frac{S_1 - S}{2S}\right)kL} \right) \quad \text{Equation 1}$$

In Equation 1, T is the power transmission, also referred to as the acoustic output, sound level, or noise level; k is the wavenumber of the sound; S1 is the area of an acoustic chamber; L is the length of an acoustic chamber; and S is the area of an inlet port or tube. Thus, if S1 increases in size, L increases in length or S decreases in area, then the power transmission T is reduced.

In accordance with the present disclosure, the area of the respective acoustic chamber (S1) and the area of its inlet port (S) may have a proportional relationship. For example, the area of the chamber may be larger than the area of the inlet port by a factor of 2. In additional embodiments, S1 may be larger than S by a factor ranging from a factor of approximately 2 to a factor of approximately 20 or more. In at least one embodiment, S1 is larger than S by a factor of about 10. Additionally, the length of L may be increased wherein the portion of the tube and the acoustic chamber effectively act as single chamber, thus decreasing the amount of noise emanating from the system.

Referring to FIG. 5, the inlet pathway defined by S is smaller than the upstream portion of the acoustic chamber. In accordance with equation 1, when S is reduced relative to S1, then T or the noise level is attenuated. By increasing L (the length of the acoustic chamber), the noise may be further attenuated. In addition, if the inlet pathway is sufficiently long, the effective length of the acoustic chamber increases from L to L1, thus also reducing the noise of the system. As illustrated in the Appendix, data supports the increase in length of intake tubes helps decrease the amount of noise escaping the system. Thus, longer inlet or sections of tubes help attenuate the noise of the system.

There exists a proportional relationship between the length of the inlet tube or port and the cross-sectional area of the inlet port with the volume (and length) of the receiving acoustic chamber. However, by increasing the length of the inlet port and restricting the cross-sectional area of the inlet port causes the resistance to air flow in the system. This may in turn cause a blower disposed inside an acoustic chamber to have to work harder, which may result in an increase in noise generation from the blower (and motor of the blower). Thus, a balancing and optimization step is often required when trying to create a sufficiently portable PAP device that is both quiet and small in size. Equation 2, illustrates this relationship of increasing modifying the various dimensions of the inlet port and the effect it has on the increased motor work and noise.

$$\text{Resistance of air flow} \propto \frac{\text{Length inlet}}{\text{Area inlet}} \propto \text{Motor Work} \propto \text{Motor Noise} \quad \text{Equation 2}$$

Another way of describing this is a smaller inlet diameter increases air flow resistance, which increases motor noise. Some practical steps have been incorporated to also position inlet ports on the PAP device such that they point away from the ears of the user. For example, in several of the figures the inlet port is on the opposite end of the outlet port and adapters, which lead to the tubing that takes air to the mask placed over the user's nose and/or mouth. In several instances most of the noise escaping the system leaves through the inlet port.

Equation 1 can also be used to describe the relationship between length and noise attenuation in an individual tube. In the case of a single, individual tube, S1 is equal to S. Accordingly, the noise output T is reduced when the tube is lengthened (L is increased). This characteristic is important because the length of the intake tube (such as intake tube 115) can be used to decrease the noise of the PAP device (such as device 100 and other systems and methods described herein).

Equation 3 describes the relationship between the cut-off frequency of the acoustic filtering and the length and areas of the chamber and tube:

$$f_c = \left( \frac{Sc}{\pi L(S_1 - S)} \right) \quad \text{Equation 3}$$

In equation 3: $f_c$ is the cutoff frequency; c is the speed of sound; S1 is the area of the expansion chamber; L is the length of the tube or chamber; and S is the area of inlet port. Thus, as L or S1 become larger in value, and/or S becomes smaller, the cutoff frequency becomes lower and every frequency above the cutoff frequency is significantly attenuated. In practical terms, the cutoff frequency $f_c$ can be reduced by increasing the ratio of S1:S, for example by decreasing the area of the inlet and/or increasing the area of the acoustic chamber. Additionally, lengthening the acoustic chamber (increase L) will also reduce the cutoff frequency.

In embodiments where the inlet ports include an intake tube, the intake tubes may extend from the furthest attenuator in the attenuating intake chamber and into the acoustic chamber. The length of the intake tube may range from approximately 1 inch to approximately 3 inches or longer. In certain approaches, the intake tube (such as intake tube 115, 215, 315, or 415) has a fixed diameter of ⅜ inch and is approximately 3 inches long. In accordance with FIG. 5, equation 1, and equation 2, the length and diameter of the intake tube may be adjusted to affect the overall noise attenuation of the PAP device. Similarly, the interchamber tube and outlet tube may be adjusted to affect the noise output of the PAP device.

In order to maximize the length of the intake tube so as to further attenuate the noise of the device, the tube may be angled, have one or more bends or turns in any 3-dimensional direction, or it may have a spiral-like configuration. For example, in FIG. 2A, FIG. 3, and FIG. 4D, the intake tube has two bends thereby creating an intake tube having an "S" shape. Similarly, interchamber tubes and outlet tubes may also include bends, turns, angles, spirals, or other configurations.

As disclosed herein, tubes within the systems described herein may be formed using rigid materials, flexible materials, or any combination thereof. For example, in some embodiments, an intake tube may be formed using a hard plastic. In other embodiments, an intake tube may be formed using flexible polyvinylchloride (PVC) tubing, silicone tubing, or any other type of tubing commonly used in the art. In certain embodiments, intake tubes are formed from more than one material.

Figure 6:
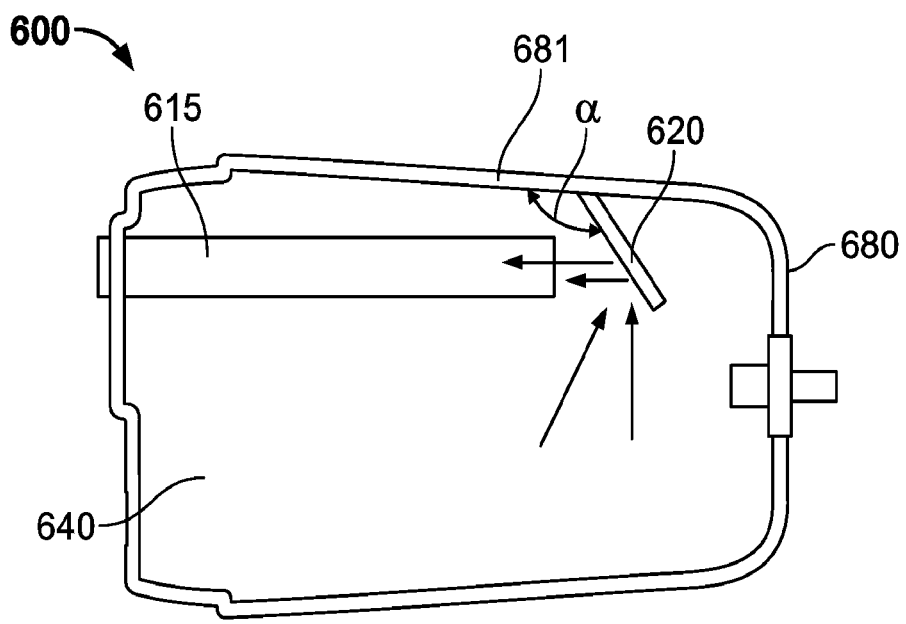
FIG. 6 illustrates a configuration of a PAP device.
Figure 7A:
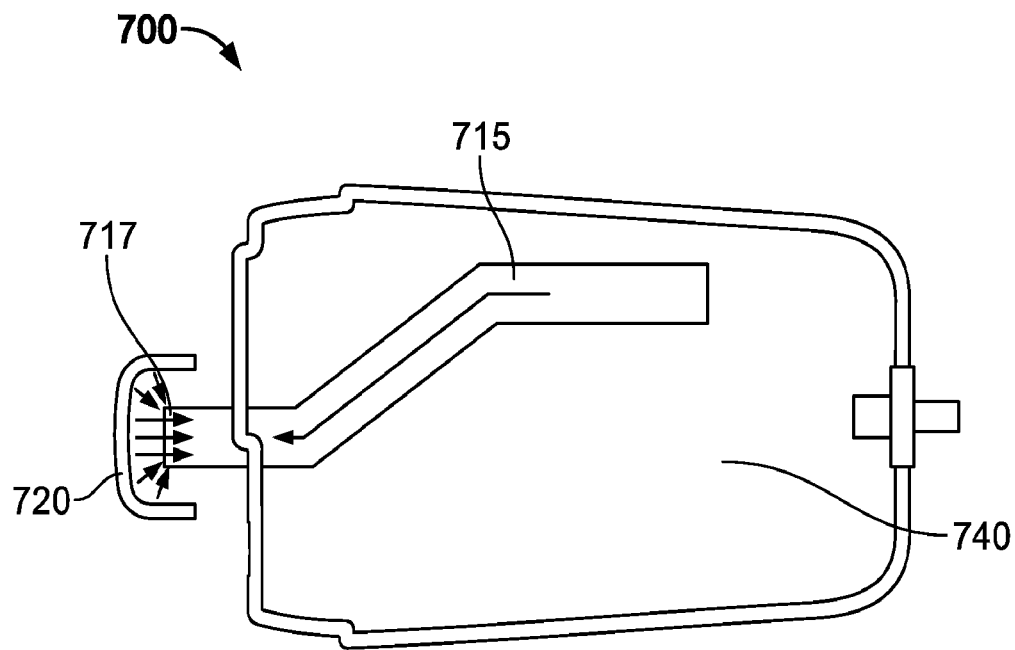
FIG. 7A and FIG. 7B illustrate additional embodiments of possible configurations of a PAP device.
Figure 7B:
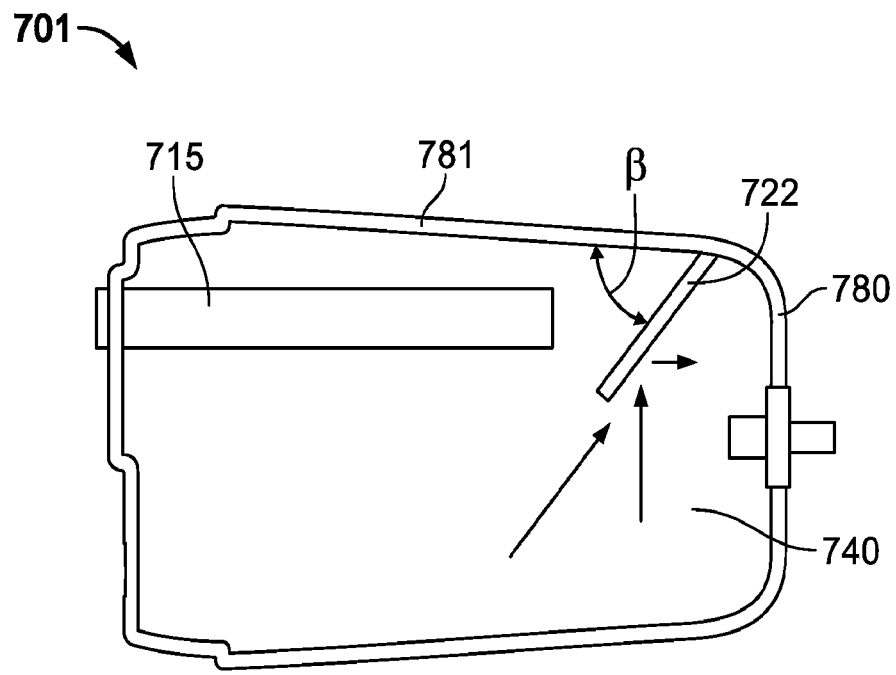

FIG. 6, FIG. 7A, and FIG. 7B depict simplified drawings to illustrate the sound deflection properties of attenuators, and accordingly, do not include all the element previously described. FIG. 6 illustrates one example of an attenuator found in previous CPAP devices. Device 600 includes an intake tube 615 leading into chamber 640 with an attenuator 620. The configuration and angle of attenuator 620 deflects sound (represented by the arrows) back through the device. The sound may be generated, for example, by the blower. Importantly, attenuator 620 is angled such that it opens towards chamber 640. For example, attenuator 620 may form an obtuse angle α with wall 681 of housing 680.

FIG. 7A depicts an end attenuator 720, which is positioned near the intake end 717 of intake tube 715. End attenuator 720 deflects sound (represented by the arrows) generated from device 700 back through tube 715 and into chamber 750 of device 700, where it can dissipate or be absorbed instead of reaching the user. End attenuator 720 may also absorb some portion of the sound. FIG. 7B illustrates a related configuration within device 701. Device 701 includes attenuator 722. Importantly, attenuator 722 is positioned such that it does not open directly toward chamber 740, unlike attenuator 620 does in relation to chamber 620. The space between tube 715 and chamber 740 is smaller near tube 715 than near wall 781 of housing 780. For example, attenuator 720 may form an acute angle β with wall 781 of housing 780. Accordingly, attenuator 720 is less likely to deflect sound waves back into tube 715. As shown by the arrows, sound waves will be deflected primarily away from tube 715 and may dissipate and be absorbed within device 701, rather than reaching the user. In certain approaches, attenuators 720 and 722 may both be used in a PAP device, and may be used with other attenuators, systems, and methods for attenuating the sound, such as tubes with bends, combinations of attenuators, and anechoic sound-reducing materials.

Figure 8A:
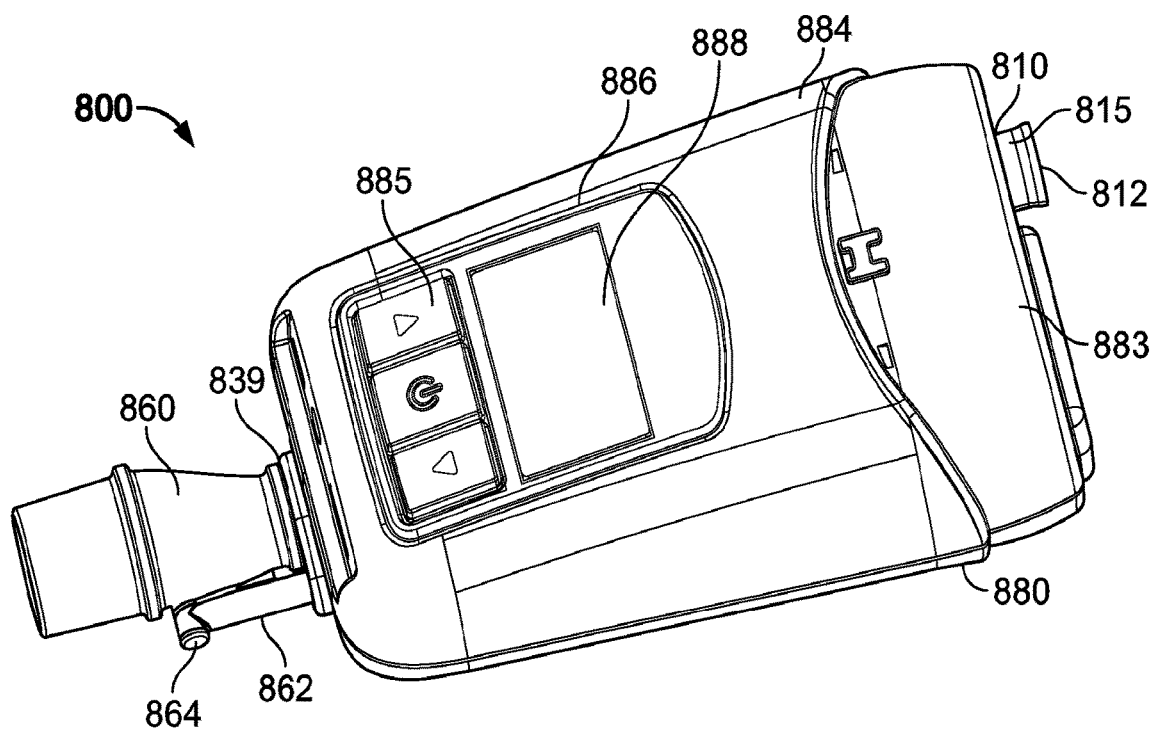
FIG. 8A and FIG. 8B illustrate a PAP device with an acoustically invisible cover.
Figure 8B:
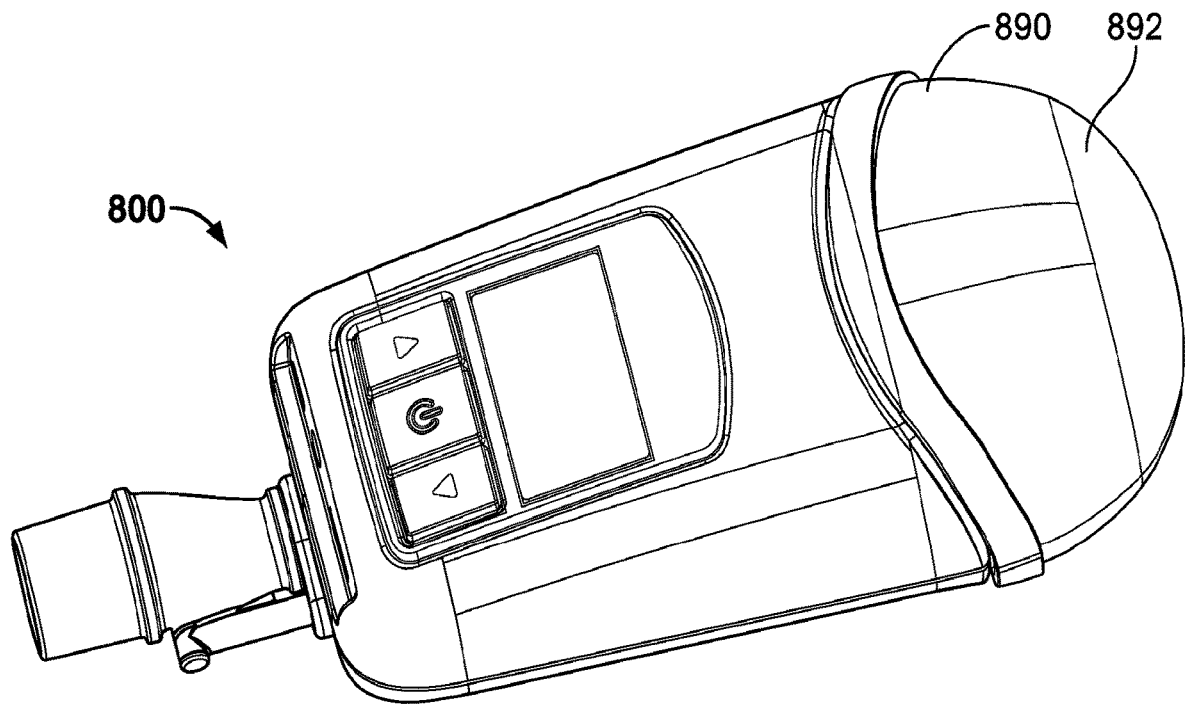

FIG. 8A and FIG. 8B depict the exterior a PAP apparatus having an internal pressure sensor. CPAP device 800 is similar to previously described CAP devices and apparatuses, such as devices 100, 200, 300, 400, 700, and 701. Device 800 has a lower housing component 880, which together with an upper housing component 884, define the interior and exterior of device 800. In certain approaches, the interior of device 800 is similar to those depicted in previous figures.

Inlet port 810 includes an intake tube 815 having a first end 812 extending through lower housing 880 and a second end (not depicted in this figure) that extends to the interior chamber (not depicted in this figure) of device 800. Intake tube 815 may have either a constant or varying internal diameter ranging from approximately 0.25 inches to approximately 0.75 inches and may have a length ranging from approximately 0.25 inches to approximately 3 inches, although any appropriate diameter and length may be used. The length and diameter of intake tube 815 affect the overall noise attenuation of the CPAP device, as previously discussed. Accordingly, in some approaches, the dimensions of intake tube 815 are proportionally related to the volume of chamber 830.

Intake tube 815 may be formed using rigid materials, flexible materials, or any combination thereof. For example, intake tube 815 may be formed using a hard plastic. In certain embodiments, intake tube 815 is composed of flexible polyvinylchloride (PVC) tubing, silicone tubing, or any other type of tubing commonly used in the art.

Device 800 includes an outlet port 839, through which device 800 provides pressurized air. An adapter 860 may be used to connect outlet port 839 to a patient interface, such as a mask.

Apparatus 800 includes a control panel 886 with digital display 888 and user interface buttons 885 for controlling and using apparatus 800. For example, a user may be able to turn the power on and off, adjust pressure settings, set a timer, run system diagnostic tests, and control or adjust other functions. Display 888 may be any appropriate display, including, but not limited to an LED or LCD display. Although 1-3 user interface buttons 885 are depicted, any appropriate number of buttons may be used. In certain approaches, a PAP apparatus, such as apparatus 800, may include between 1 and 10 user interface buttons. In certain approaches, user interface buttons are included in display 888. For example, display 888 may be a capacitive or pressure sensitive touch screen display. Further, control panel 886 and display 888 may vary in size between different embodiments. For example, some embodiments may include a larger display, while other embodiments may include a smaller display. Display 888 may display data or control functions, such as pressure levels, time, use time, or other information. Display 888 may show one piece of data or function or a plurality of data and functions.

In certain embodiments, apparatus 800 includes a pressure port 862. Pressure port 862 has a first end 864 on the exterior of lower housing 880 and upper housing 884. First end 864 is coupled to adapter 860. Pressure port 862 provides fluid communication from the output of device 800 at adapter 860 to a pressure sensor within device 800. In certain approaches, the pressure sensor is coupled to control circuitry (not depicted) within device 800. The control circuitry of device 800 is configured to display the pressure measured through pressure port 862 at display 888 of control panel 886 on upper housing 884.

In certain embodiments, the pressure output of device 800 may be adjusted manually by the user with user interface buttons 885. In certain approaches, the control circuitry of device 800 is configured to automatically adjust the output of device 800 based on the pressure measurements. The output of device 800 may be adjusted, for example, by modulating the power of the blower.

During operation, PAP device 800 creates positive air pressure through outlet port 839. For example, when a patient interface is attached to adapter 860, PAP device 800 creates positive air pressure, which can be provided to the patient when the patient places an adapter, such as a mask, at his or her airways (e.g., nose or mouth).

As depicted in FIG. 8B, device 800 may include an intake cover 890. In certain embodiments, air may be passed through intake cover 890 before entering inlet port 810. Intake cover 890 serves to prevent the occlusion of inlet port 810 during use of device 800. Intake cover 890 includes a vented portion 892 to allow the pass through of air during operation of device 800. In certain embodiments, intake cover 890 may include a filter to clean the air of particulate matter. In certain embodiments, intake cover 890 is removable so that it may be cleaned, replaced, or adapted for a particular need. In certain embodiments, intake cover 890 includes attenuators, such as those previously described.

In certain approaches, the pressurized air is delivered to a patient through a patient interface at a pressure ranging from approximately 2 centimeters (cm) of water to approximately 40 cm of water above atmospheric pressure at the point of use, although any appropriate pressure may be used.

Figure 9A:
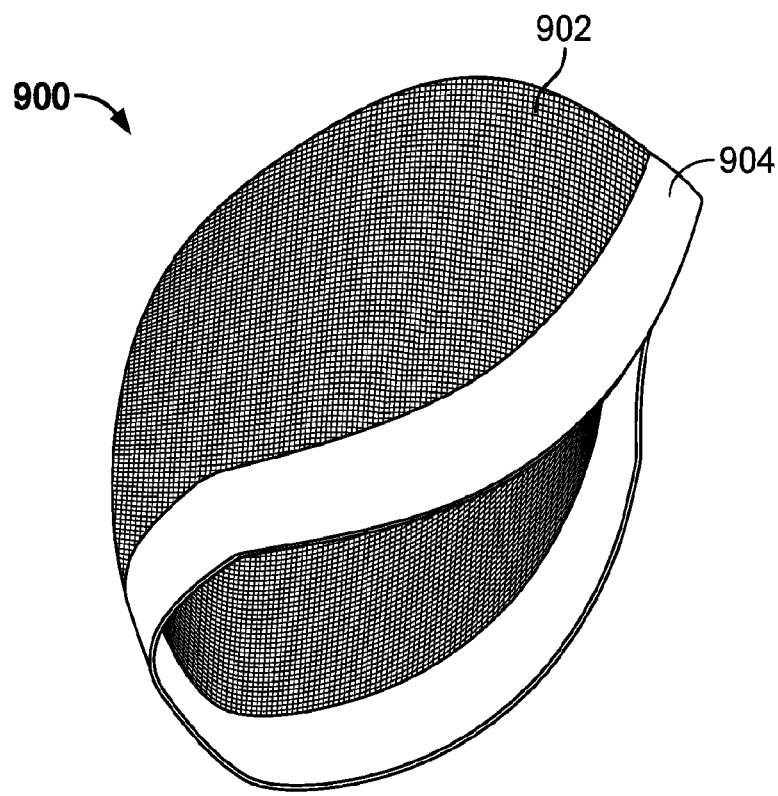
FIGS. 9A-B depict an acoustically invisible cover.

FIG. 9A depicts one embodiment of an acoustically invisible cover 900. Cover 900 may be similar to cover 890 and is positioned on the housing over the inlet port (such as inlet ports 122, 222, 322, 410, or 810) to prevent occlusion of the inlet port during use. Cover 900 includes a first portion 904, which is shaped similar to the housing of a PAP device (such as devices 100, 200, 300, 400, 700, 701, and 800) so that it can couple directly to the housing. Cover 900 includes a flow portion 902, which is sufficiently porous so that air can flow through it. In certain embodiments, flow portion 902 is constructed of a mesh material, such as a metal or plastic. For purposes of this application acoustically invisible refers to not increasing the generated noise by more than 3 dBA. Ideally the increase in dBA is less than 1 dBA, less than 0.5 dBA and negligible.

Figure 9B:
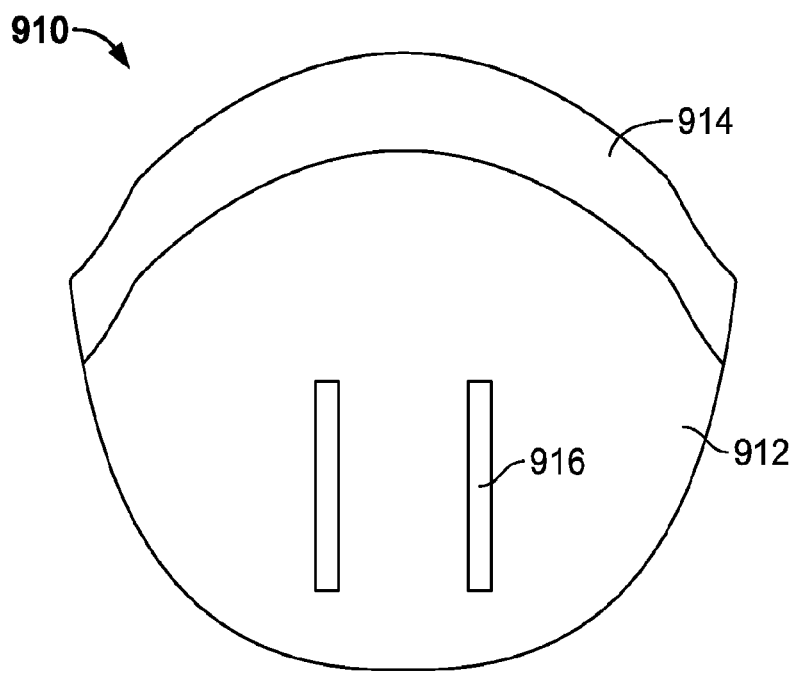

FIG. 9B depicts an embodiment of an acoustically invisible cover 910. Cover 910 may be similar to cover 890 or cover 900 and is positioned on the housing over the inlet port (such as inlet ports 122, 222, 322, 410, or 810) to prevent occlusion of the inlet port during use. Cover 910 includes a first portion 914, which is shaped similar to the housing of a PAP device (such as devices 100, 200, 300, 400, 700, 701, and 800) so that it can couple directly to the housing. Cover 910 includes flow portion 912, which is sufficiently porous so that air can flow through it. For example, flow portion 912 may be constructed of paper or mesh. In certain approaches, flow portion 912 includes vents such as vents 916. In a design where flow portion 912 is not porous and solid the vents 916 may actually increase the dBA, such that it is no longer acoustically invisible.

In certain embodiments, intake cover 900 and intake cover 910 include attenuators, such as those previously described in relation to PAP devices 100, 200, 300, 400, 700, 701, and 800.

In the absence of any additional outside attenuators, the CPAP device disclosed herein, having one interior attenuator, produces noise levels of about 27 dBA.

The above description is merely illustrative. Having thus described several aspects of at least one embodiment of this invention including the preferred embodiments, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only.

What is claimed is:

1. A noise attenuating system for use with ventilation or other systems providing a flow of gas comprising:
   an expansion chamber, an intake tube, an intake chamber, and a plurality of acoustic deflectors;
   wherein the intake tube comprises an inlet port and an outlet port separated by a length, wherein the inlet port of the intake tube extends outside of the expansion chamber into the intake chamber;
   wherein the intake chamber comprises an intake vent and a noise attenuator;

wherein the noise attenuator comprises a bottom and protruding sidewall forming a cavity and the plurality of acoustic deflectors are disposed within the cavity of the noise attenuator;

wherein at least one of the plurality of acoustic deflectors extends from the sidewall and is aligned substantially parallel to the bottom of the noise attenuator;

wherein the intake vent, the noise attenuator, and the inlet port of the intake tube are configured to create an airflow path with at least two right-angle turns; and wherein the inlet port of the intake tube extends into the cavity of the noise attenuator and the noise attenuator is configured to deflect sound from the expansion chamber away from the intake vent.

2. The system of claim 1, wherein the intake tube length ranges from 0.25 inches to 3.5 inches.

3. The system of claim 1, wherein at least one of the plurality of acoustic deflectors extends from the sidewall and is angled into the cavity of the noise attenuator.

4. The system of claim 1, comprising a noise dissipating element disposed within the cavity of the noise attenuator.

5. The system of claim 4, wherein the noise dissipating element is a porous material.

6. The system of claim 1, wherein a portion of at least one of the plurality of acoustic deflectors is covered by a noise dissipating material.

7. A device for treating an upper airway occlusion, comprising an expansion chamber, an intake tube, an intake chamber, and a plurality of acoustic deflectors;

wherein the intake tube comprises an inlet port and an outlet port separated by a length, wherein the inlet port of the intake tube extends outside of the expansion chamber into the intake chamber;

wherein the intake chamber comprises an intake and a noise attenuator;

wherein the noise attenuator comprises a bottom and protruding sidewall forming a cavity and the plurality of acoustic deflectors are disposed within the cavity of the noise attenuator;

wherein at least one of the plurality of acoustic deflectors extends from the sidewall and is aligned substantially parallel to the bottom of the noise attenuator;

wherein the intake vent, the noise attenuator, and the inlet port of the intake tube are configured to create an airflow path with at least two right-angle turns; and wherein the inlet port of the intake tube extends into the cavity of the noise attenuator and the noise attenuator is configured to deflect sound generated from the device away from the intake vent.

8. The device of claim 7, wherein the intake tube length ranges from 0.25 inches to 3.5 inches.

9. The device of claim 7, wherein at least one of the plurality of acoustic deflectors extends from the sidewall and is angled into the cavity of the noise attenuator.

10. The device of claim 7, comprising a noise dissipating element disposed within the cavity of the noise attenuator.

11. The device of claim 10, wherein the noise dissipating element is a porous material.

12. The device of claim 7, wherein a portion of at least one of the plurality of acoustic deflectors is covered by a noise dissipating material.

* * * * *